United States Patent [19]

Cocker

[11] 4,014,872
[45] Mar. 29, 1977

[54] SUBSTITUTED 3-HYDROXY- OR 3-OXO-CEPHAMS

[75] Inventor: John Derek Cocker, Chalfont St. Peter, England

[73] Assignee: Glaxo Laboratories Limited, Greenford, England

[22] Filed: Jan. 3, 1974

[21] Appl. No.: 430,386

[52] U.S. Cl. .................... 260/243 C; 260/239 A; 260/239 EP; 260/247.1 M; 260/250 Q; 260/293.68; 260/294.8 C; 260/306.7 R
[51] Int. Cl.[2] .................................. C07D 501/14
[58] Field of Search .............. 260/243 C, 306.7 R

[56] References Cited
UNITED STATES PATENTS 3,842,072  10/1974  Heusler et al. ............... 260/243 C

*Primary Examiner*—Nicholas S. Rizzo
*Assistant Examiner*—David E. Wheeler
*Attorney, Agent, or Firm*—Bacon & Thomas

[57] ABSTRACT

The invention relates to novel semisynthetic intermediates or relay compounds of use in the production of cephalosporins and related β-lactam antibiotic compounds. The novel compounds are 3-hydroxy- and 3-oxo-7-amino- and blocked amino —(6R,7R)-cephams. Process for the preparation of the novel compounds are described and exemplified.

4 Claims, No Drawings

SUBSTITUTED 3-HYDROXY- OR 3-OXO-CEPHAMS

This invention relates to a process for the production of novel semisynthetic intermediates or relay compounds of use in the production of cephalosporins and related β-lactam antibiotic compounds.

The first reported total synthesis of a cephalosporin used as starting material L(+)-cysteine. However, the conversion of this material into a β-lactam of the required stereochemical configuration requires extremely careful control of the stereochemistry at several points.

In Belgian Patents Nos. 770726, 770727, 770728, 770729 and 770730 we have described inter alia the production from penicillins of compounds which can be represented by the formula

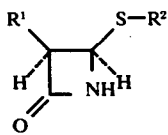
I where $R^1$ is an amino group or a blocked amino group, including in particular groups —NHCOR which are sidechains present in the 6-position in penicillins; and $R^2$ is an acyl group (including a sulphonyl, sulphinyl or phosphoryl group); or the residue —S.$R^3$ of a thiophilic sulphur nucleophile $R^3$SH; or $R^2$ is a group of the formula

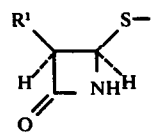
II;

or $R^1$ and $R^2$ together with the sulphur atom form a group

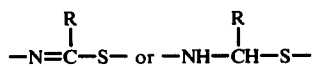

The compounds of formula I possess the β-lactam ring structure of the penicillins from which they were derived, with the same steric configuration. They are thus very suitable intermediates for the production of β-lactam antibiotics such as further penams and the related cephams and cephems.

Belgian Patent No.770731 (Part 9) describes the reaction of a compound of formula I with a reactive ester of an alcohol or phenol, with an acylating agent or with an aliphatic or araliphatic compound containing an electrophilic multiple carbon-carbon bond, in the presence of a base able to deprotonate the β-lactam nitrogen, to give compounds analogous to those of formula I but having attached to the β-lactam nitrogen atom(s) an aliphatic, aromatic, araliphatic or acyl group. Following functionalisation of the group attached to the β-lactam nitrogen atom, such compounds may cyclise to give bicyclic structures of the penam, cepham or cephem type which can then be readily converted either into active antibiotics of known activity previously obtained by more difficult synthesis or into new active antibiotics. Thus, for example, one new class of active antibiotics described in the foregoing Patent specifications are the 2-carboxypenams.

We have now found methods similar to those described in Belgian Patent No. 770731, whereby a further new class of cephams can be obtained, namely 3-hydroxy or 3-oxo-7-amino- or blocked amino -(6R,7R)-cephams.

These in general can be represented by the formula:

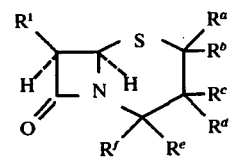
III wherein $R^1$ is as defined above; $R^a$, $R^b$, $R^e$ and $R^f$, which may be the same or different, represent hydrogen atoms or alkyl, aralkyl, aryl, cyano or carboxyl or blocked carboxyl groups; and $R^c$ represents a hydroxy group and $R^d$ represents a hydrogen atom or $R^c$ and $R^d$ together represent an oxygen atom. These can be converted into related cephams by known techniques such as oxidation and condensation reactions in order to produce β-lactam antibiotics. These may have at the 7-position a group $R^1$ as defined above.

The new 3-hydroxy and 3-oxo cephams can be prepared by cyclisation of suitably substituted azetidin-2-ones. Thus, in general, they may be prepared by cyclising compounds of the formula

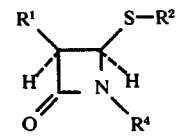
IV

[wherein either (a) $R^1$ represents a free or blocked amino group, $R^2$ represents a group of formula

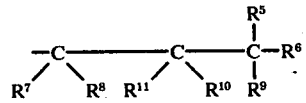
V (where $R^5$, $R^6$, $R^7$ and $R^8$, which may be the same or different, each represents a hydrogen atom or an alkyl, aralkyl, aryl, cyano or free or blocked carboxyl group; and $R^9$ and $R^{10}$ together represent a divalent oxygen atom and $R^{11}$ represents hydrogen or $R^9$ represents hydrogen or a readily eliminable substituent and $R^{10}$ and $R^{11}$ together represent a divalent oxygen atom) and $R^4$ represents a hydrogen atom; or (b) either $R^1$ represents a free or blocked amino group and $R^2$ represents an acyl group (including a sulphonyl, sulphinyl or phosphoryl group), the residue —S$R^3$ of a thiophilic sulphur nucleophile $R^3$SH (where $R^3$ is an aliphatic, araliphatic or aromatic group) or a group of formula

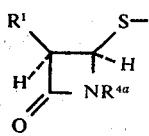   IIa (where $R^{4a}$ is hydrogen or a group $R^4$), or $R^1$ and $R^2$ together with the sulphur atom to which $R^2$ is attached represent a group

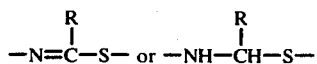

where R is a residue of an acyl group RCO containing 1 to 20 carbon atoms; and $R^4$ represents a group of formula V].

The compounds of formula IV may themselves be obtained from compounds of the formula I by reaction with a compound of the formula

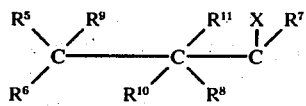   VI (where $R^5$, $R^6$, $R^7$, $R^8$, $R^9$, $R^{10}$ and $R^{11}$ have the above meanings and X is a readily eliminable substituent) whereby a group of formula V is added at the S-atom or the N-atom according to the reaction conditions employed.

Reaction at the N-atom

The conditions for reaction of the compound of formula VI with the N-atom of the compound of formula I are the same as those for the cyclisation of a compound of formula IV wherein $R^4$ is hydrogen and $R^2$ is a group of formula V. In general, reaction at the N-atom takes place under basic reaction conditions whereby the β-lactam nitrogen is deprotonated. Bases which may be present include, for example, alkali metal carbonates, e.g. sodium or potassium carbonate, in which case the medium may contain some water; alkali metal hydrides, amides or silylamides e.g. sodium or potassium hexamethyldisilanazyl; tertiary organic bases such as trialkyl amines which are sufficiently hindered to impede alkylation of the tertiary base; or quaternary ammonium bases, e.g. N,N,N-trimethyl-N-benzylammonium hydroxide.

An inert solvent is preferably present, advantageously a polar solvent e.g. a ketone such as acetone or methyl ethyl ketone, a cyclic ether such as dioxan or tetrahydrofuran, or an amide or imide solvent such as dimethylformamide or dimethylacetamide.

Reaction at the S-atom

The conditions for reaction of the compound of formula VI with the S-atom of the compound of formula I are the same as those for the cyclisation of a compound of formula IV in which $R^4$ is a group of formula V. In general the reaction may be effected, where $R^1$ and $R^2$ do not form a group

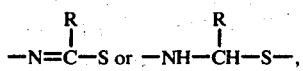

by methods analogous to those described in Belgian Patent No. 770730. Where $R^2$ is a group —S—$R^3$ or a group of formula II, the —S.S— bond may be subjected to reductive cleavage e.g. by reducing agents or hydrolysis whereby electrons are introduced, or by a thiophilic nucleophile which also provides electrons; in such a case a transient intermediate is thought to be the thiolate anion which reacts subsequently with the etherifying agent.

Thus, for example, the disulphide can be reacted with a trivalent phosphorus compound to effect the desired cleavage. This reagent can be represented as $PR^{12}R^{13}R^{14}$ where $R^{12}$ and $R^{13}$, which may be the same or different, are hydrocarbyl, hydrocarbyloxy or hydrocarbylamino groups, e.g. alkyl, alkoxy or dialkylamino groups, preferably having 1–6 carbon atoms such as methyl, ethyl, t-butyl, methoxy or ethoxy groups; aralkyl, aralkoxy or diaralkylamino groups, preferably monocyclic groups with 1—6 carbon atoms in the alkyl portion, such as benzyl, phenethyl, benzyloxy or phenethoxy groups; or aromatic groups, preferably monocyclic groups, such as phenyl, tolyl, phenoxy or tolyloxy groups or diarylamino groups; or $R^{12}$ and $R^{13}$ may together with the phosphorus atom form a ring: and $R^{14}$ is another group as defined for $R^{12}$ and $R^{13}$ or a hydroxyl group. Particular reagents of this type are the di- and tri- alkyl phosphites, preferably the latter, and the trisubstituted phosphines; convenient reagents are tri-n-butyl and tri-n-octyl phosphines and trimethyl and triethyl phosphite. The compound $P(NMe_2)_3$ is a convenient reagent of the tri-(hydrocarbylamino) phosphine type.

The reaction with phosphorus-based reagents is preferably effected at between 0° and 120° C, conveniently in the range 15° to 50° C.

In general, an inert solvent is preferably present, for example a cyclic ether solvent such as dioxan or tetrahydrofuran, an ester solvent such as ethyl acetate, or a hydrocarbon solvent such as benzene or toluene. A small quantity of a hydroxylic substance is preferably present e.g. water.

Selective reduction of the —S—S— bond can also be effected using electrolysis or reagents such as hydrogen iodide or more particularly, hydride reducing agents. Such reagents should not attack other parts of the molecule and we have found borohydrides especially suitable, particularly alkali metal borohydrides such as sodium or potassium borohydride. Borohydrides may be used in hydroxylic solvents such as alkanols, e.g. methanol, ethanol etc. and/or water.

Cleavage can also be effected using thiophilic sulphur nucleophiles and in particular thiols, including substances such as thiourea and other thioamides, thiophosphates, thiosulphates, sulphites, sulphinates, thiocyanates and thioglycollates which can react as thiols, and hydrogen sulphide. The thiols or hydrogen sulphide are preferably reacted either in the presence of a base or as salts with bases. Such bases include inorganic bases, in particular alkali metal compounds e.g. sodium, potassium or lithium compounds, for example hydroxides, alkoxides, and hydrides and organic bases such as amines e.g. triethylamine or quaternary ammonium hydroxides. Cleavage can additionally be effected by cyanides. The foregoing thiophosphates, thiosulphates, sulphites, sulphonates, thiocyanates and cyanides are preferably alkali metal, e.g. sodium or potassium, or quaternary ammonium salts.

When $R^1$ and $R^2$ together form a group

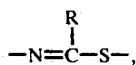

the reaction may be effected in the presence of a thallium triacylate or a weak base having a $pK_a$ of less than 10 (in water at 25° C), e.g. urea, and a hydroxylated compound.

Where the hydroxylated compound produces ions other than hydroxyl ions, the initial product may, in the absence of water, be an imino ether rather than an amide and treatment with a protic solvent such as water will be required to generate the amide. The hydroxylated compound may, for example, be an alkanol such as methanol or ethanol. In general, it is preferred that sufficient water should be present during the reaction to form the amide directly. Suitable solvent media include alkanols such as ethanol or methanol, ketones such as acetone or methyl ethyl ketone, cyclic ethers such as dioxan or tetrahydrofuran or amide, imide or hydantoin solvents such as dimethylformamide and dimethylacetamide.

Where $R^1$ and $R^2$ together form a grouping

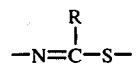

or a corresponding thiazolidine grouping

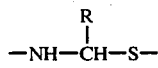

the reaction may be effected in the presence of an acid, e.g. a mineral acid, such as phosphoric or sulphuric acid or a carboxylic acid such as formic, acetic or propionic acid, advantageously in the presence of a protic solvent such as water or an amide solvent such as dimethylformamide, and in the presence of electrophilic promoters as derived from metallic salts, e.g. of Zn and Mg, specifically $Zn(OAc)_2$. Lewis acids such as trialkyl borates or phosphorus trihalides may also be used; normally an aprotic solvent is used, in which case aqueous workup may be needed to liberate 3-hydroxylated products from initially formed complexes.

Where $R^2$ is an acyl group, cleavage can be effected by treatment with a base. In the initial reaction between compounds I and VI this may cause reaction both at the N- and S-atoms. In general, the base may, for example, be an alkali metal hydroxide or alkoxide.

The compounds of formula IV are new compounds, and constitute a further feature of the invention.

The compound of formula I is preferably a thiazoline, i.e. $R^1$ and $R^2$ together with the sulphur atom preferably constitute a group

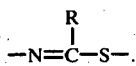

The group X of the compound of formula VI is advantageously a bromine, chlorine or iodine atom or a hydrocarbonsulphonyloxy group such as a mesyloxy or tosyloxy group. Where $R^2$ is a readily eliminable group, this also is advantageously a bromine, chlorine or iodine atom or such a hydrocarbon-sulphonyloxy group.

The compound of formula VI is advantageously a compound having a molecular weight of not greater than 600. Preferred compounds of formula VI are those wherein $R_5$, $R_6$, $R^7$ and $R_8$ all represent hydrogen atoms.

In the above formulae, $R^1$ is an amino group or a blocked amino group. As used herein, the term "blocked" means that the group which is blocked carries at least one substituent and is no longer a free amino, carboxyl or hydroxyl group. The term "protected" as used herein means that the group concerned carries at least one substituent which can be removed selectively without undue damage to the rest of the molecule, e.g. by hydrolysis, hydrogenolysis or reduction.

$R^1$ may thus be a protected amino group and this may conveniently be one of the groups set out in the following table:

| Type | Example | Usual Name and Analogous etc. |
|---|---|---|
| Urethane | HNCOCH$_2$Ph ‖ O | Benzyloxycarbonyl, p-Methoxy |
| Urethane | HNCOC(CH$_3$)$_3$ ‖ O | t-Butoxycarbonyl |
| Urethane | HNCOCHPh$_2$ ‖ O | Diphenylmethoxycarbonyl |
| Urethane | HNCO— (1-adamantyl) ‖ O | Adamantyloxycarbonyl |
| Arylmethylamino | HNCPh$_3$ | Trityl |
| Urethane | HN . CO . OCH$_2$CCl$_3$ | β,β,β-trichloroethoxycarbonyl |
| Imide | —N(CO)$_2$C$_6$H$_4$ | Phthaloyl |

Where $R^1$ is a group NHCOR, R can be defined generally as hydrogen or an organic group which preferably contains 1–20 carbon atoms.

In general, the following main classes are of interest for the acyl group RCO-:

i. $R^uC_nH_{2n}$-CO where $R^u$ is aryl (carbocyclic or heterocyclic), cycloalkyl, substituted aryl, substituted cycloalkyl, cyclohexadienyl, or a nonaromatic or mesoionic heterocyclic group, and n is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis (2-chloroethyl)aminophenylpropionyl; thienyl-2-and -3-acetyl; 4-isoxazolyl and substituted 4-sioxazolylacetyl; pyridylacetyl; tetrazolylacetyl or a sydnonacetyl group. The substituted 4-isoxazolyl group may be a 3-aryl-5-methyl isoxazol-4-yl group, the aryl group being e.g. phenyl or halophenyl e.g. chloro- or bromophenyl. An acyl group of this type is 3-o-chlorophenyl-5-methylisoxazol-4-yl-acetyl. ii. $C_nH_{2n+1}$CO- where n is an integer from 1-7.

The alkyl group may be straight or branched and, if desired, may be interrupted by an oxygen or sulphur atom or substituted by e.g. one or more halogen atoms, a cyano group, a carboxy group, an alkoxycarbonyl group, a hydroxy group or a carboxycarbonyl group (—CO.COOH). Examples of such groups include cycanoacetyl, hexanoyl, heptanoyl, octanoyl, butylthioacetyl, chloroacetyl and trichloroacetyl groups.

iii. $C_nH_{2n-1}CO$— where n is an integer from 2-7. The alkenyl group may be straight or branched and, if desired, may be interrupted by an oxygen or a sulphur atom. An example of such a group is allylthioacetyl.

iv.

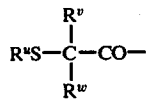

where $R^u$ has the meaning defined under (i) and in addition may be benzyl, and $R^v$ and $R^w$ which may be the same of different each represent hydrogen, phenyl, benzyl, phenenethel or lower alkyl. Examples of such groups include phenoxyacetyl, 2-phenoxy -2-phenylacetyl, 2-phenoxypropionyl, 2-phenoxybutyryl, 2-methyl-2-phenoxypropionyl, p-cresoxyacetyl and p-methylthiophenoxyacetyl.

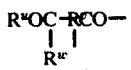

v. where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

vi. $R^uZ(CH_2)_mCO$— where $R^u$ has the meaning defined under (i) and, in addition, may be benzyl, Z is an oxygen or sulphur atom and m is an integer from 2–5. An example of such a group is S-benzylthiopropionyl.

vii. $R^uCO$— where $R^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl), quinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower)alkyl amido, morpholinocarbonyl, pyrrolidinocarbonyl, piperidinocarbonyl, tetrahydropyridino, furfurylamido or N-alkyl-N-anilino, or derivatives thereof and such substituents may be in the 2- or 2- and 6-positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol-4-yl carbonyl, 3-o-chlorophenyl-5-methyl isoxazol-4-yl carbonyl and 3-(2,6-dichlorophenyl)-5-methyl-isoxazol-4-yl carbonyl.

viii.

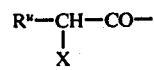

where $R^u$ has the meaning defined under (i) and X is amino, substituted amino (e.g. acylamido or a group obtained by reacting the α-amino-acylamido group of the 6-side chain with an aldehyde or ketone e.g. acetone, methylethylketone or ethyl acetoacetate), hydroxy, carboxy, esterified carboxy, triazolyl, tetrazolyl, cyano, halogeno, acyloxy (e.g. formyloxy or lower alkanoyloxy) or etherified hydroxy group. Examples of such acyl groups are α-aminophenylacetyl and α-carboxyphenylacetyl.

ix.

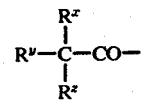

where $R^x$, $R^y$ and $R^z$ which may be the same or different may each represent lower alkyl, phenyl or substituted phenyl. $R^x$ can also be hydrogen. An example of such an acyl group is triphenylmethylcarbonyl.

x.

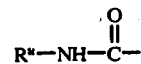

where $R^u$ has the meaning defined under (i) and in addition may be hydrogen, lower alkyl or halogen substituted lower alkyl. An example of such a group is $Cl(CH_2)_2NHCO$.

xi.

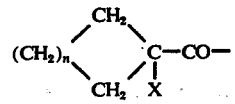

where X has the meaning defined under (viii) above and n is an integer of from 1 to 4. An example of such an acyl group is 1-aminocyclohexanecarbonyl.

xii. Amino acyl, for example $R^uCH(NH_2).(CH_2)_nCO$, where n is an integer from 1-10, or $NH_2$.$C_nH_{2n}Ar(CH_2)_mCO$, where m is zero or an integer from 1-10, and n is 0, or 2, $R^w$ is a hydrogen atom or an alkyl, aralkyl, or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the p-aminophenylacetyl group. Other acyl groups of this type include those, e.g. δ-aminoadipoyl, derived from naturally occurring amino acids and derivatives thereof e.g. N-benzoyl-δ-aminoadipoyl or N-chloroacetyl-δ-aminoadipoyl.

xiii. Substituted glyoxylyl groups of the formula $R^y$.CO.CO— where $R^y$ is an aliphatic, araliphatic or aromatic group, e.g. a thienyl group, a phenyl group, or a mono-, di- or tri- substituted phenyl group, the substituents being, for example, one or more halogen atoms (F, Cl, Br or I), methoxy groups, methyl groups or amino groups, or a fused benzene ring. Included in this group are also the α-carbonyl derivatives of the above substituted glyoxylyl groups, formed for example with hydroylamino, semicarbazide, thiosemicarbazide, isoniazide or hydrazine.

xiv. Formyl or haloformyl, e.g. chloroformyl.

xv.

(having syn or anti configuration)
wherein $R^z$ is a cyano group or a substituted or unsubstituted aryl (carbocyclic or heterocyclic) group or a cycloalkadienyl group and $R^a$ is a. hydrogen; or
b. carboxylic acyl e.g. an aliphatic, cycloaliphatic or aromatic acyl group, or an acyl group in which the carbonyl group is linked to an aliphatic, cycloaliphatic or aromatic group through an oxygen or sulphur atom or through an imino group. Representative of such groups are alkanoyl, alkenoyl, alkynoyl, alkoxycarbonyl, alkylthiocarbonyl, aralkoxycarbonyl, aroyl, carbamoyl and thiocarbamoyl groups, all of which may carry substituents; or
c. a monovalent organic group linked to the oxygen atom through a carbon atom e.g. a lower alkyl group, an alkenyl group, an alkynyl group, a cycloalkyl group, a cycloalkenyl group, a carbocyclic or heterocyclic aryl lower alkyl group, a carbocyclic aryl group or a heterocyclic aryl group, all of which may carry substituents. Examples of groups $R^z$ include phenyl, naphthyl, thienyl, furyl, pyridyl, oxadiazolyl and isoxazolyl and substituted derivatives thereof carrying, for example, one or more hydroxy, halogeno (Cl, F or Br), amino, nitro, aklyl, alkoxy, phenyl or halophenyl atoms or groups.

Preferred amino protecting groups are the hydrocarbyloxycarbonyl groups (wherein the amino group forms part of a urethane) in particular alkoxycarbonyl groups such as methoxycarbonyl, ethoxycarbonyl and, most preferably t-butoxycarbonyl groups, which may carry substituents such as halogen atoms as in the 2,2,2-trichloroethoxycarbonyl group, as well as aralkoxycarbonyl groups such as benzyloxycarbonyl, p-methoxybenzyloxycarbonyl and diphenylmethoxycarbonyl groups. Cycloalkoxycarbonyl groups are also advantageous, especially the adamantyloxycarbonyl group. The p-nitrobenzyloxycarbonyl group, which can be selectively removed by reduction e.g. hydrogenolysis, is also useful. The initial penicillins carrying protecting groups of this type may be prepared from 6-aminopenams by conventional methods for example by reaction with an appropriate haloformic ester.

$R^2$, when an acyl group, may be an aliphatic, araliphatic or aromatic acyl group, preferably having 1-20 carbon atoms, e.g. a lower ($C_{1-5}$) aliphatic acyl group such as an acetyl or propionyl group; a monocyclic aralkanoyl group, preferably having 1-6 carbon atoms in the alkyl portion, e.g. a phenacetyl or phenylpropionyl group; or a monocyclic aroyl group, e.g. benzoyl or toluoyl group.

Where $R^2$ is $-SR^3$, $R^3$ is preferably an aliphatic, araliphatic, or aromatic group containing 1 to 20 carbon atoms, for example an alkyl group (e.g. a $C_{1-5}$ alkyl group) such as a methyl, ethyl or butyl group; an aralkyl group, preferably a monocyclic aralkyl group having 1 to 5 carbon atoms in the alkyl portion, e.g. a benzyl, phenethyl or triphenylmethyl group; or a monocyclic aryl group such as a phenyl or tolyl group.

The hydroxycephams obtained by cyclisation of the compounds of formula IV may subsequently be converted into the corresponding 3-oxocephams by conventional oxidative methods. Thus, for example, oxidation may conveniently be effected by means of dimethylsulphoxide in the presence of acetic anhydride or a carbodiimide e.g. dicyclohexylcarbodiimide, by means of ruthenium tetroxide or by means of aluminium isopropoxide or by means of a chromium trioxide oxidising agent, e.g. chromium trioxide/pyridine.

The 4-unsubstituted-3-oxo compounds of the present invention, for example the compounds of formula III in which $R^c$ and $R^d$ are oxygen and $R^e$ and $R^f$ are hydrogen may be used as intermediates in the preparation of compounds of the cephalosporin type having anti-bacterial actvity. They may, for example, be subjected to base-catalysed alkoxycarbonylation to introduce an alkoxycarbonyl group at the 4-position, followed by reduction of the 3- keto group to hydroxyl, elimination of the latter to introduce a 3,4-double bond and deesterification 3-Unsubstituted ceph-3-em-4-carboxylic acids have been shown in German Application No. 2151567 to be useful antibiotic substances; where a 4-carbonyl group is already present, elimination of a 3-hydroxyl group will give a 3,4-double bond to provide such an antibiotic directly.

The following Examples illustrate the present invention. The integrals for the pmr signals agreed with expectation except where stated otherwise. Signs for the coupling constants (J) have not been deduced. Temperatures are in degrees Celsius. By "epibromohydrin" is meant DL-oxiran-2-ylmethyl bromide.

EXAMPLE 1

(1R,5R,2¹R and S)-3-Benzyl-7-(oxiran-2¹-ylmethyl)-4-7-diaza-6-oxo-2-thiabicyclo-[3,2,0]-hept-3-ene

A solution of (1R,5R)-3-benzyl-4,7-diaza-6-oxo-2-thiabicyclo-[3,2,0]-hept-3-ene (1.09 g., 5 mmole) in N,N-dimethylformamide (20 ml.) was treated at 5° with sodium hexamethylsilazide (0.96 g., 5.25 mmole). To the resultant deep-red solution was added epibromohydrin (4.0 ml., 49 mmole). After a period of 3 minutes the reaction was partitioned between ethyl acetate and water. The organic phase was washed with water and brine, and dried over sodium sulphate. Removal of the solvent gave a semi-solid (1.63 g.) which was extracted with boiling either (2 × 150 ml.). Removal of the ether gave a solid which was crystallized from isopropyl alcohol to give (1R,5R,2¹R and S)-3-benzyl-7-(oxiran-2¹-yl-methyl-4,7-diaza-6-oxo-2-thiabicyclo-[3,2,0]-hept-3- ene, as needles (0.74 g., 54%), m.p. 97° to 98.5° (Mettler), $[\alpha]_D^{18}$ − 46.6° (c, 1.05, $CHCl_3$), inflexion (EtOH) at 238 nm ($\epsilon$ 2080), $\nu_{max.}$ (nujol) 1752 ($\beta$-lactam), 1613, 1601 and 1499 (aromatic) and 1255, 950 and 925 cm$^{-1}$ (epoxide), NMR ($C_6D_6$, $\tau$) 2.85 ($C_6H_5$), 4.45 (m, 5-H), 5.02 and 5.14 (pair of doublets, J 4 Hz., 1-H), 6.4 ($PhCH_2$), 6.7 to 7.4

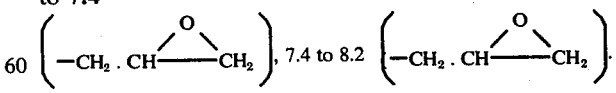

The diastereoisomers appeared to be present in nearly equal proportions. (Found: C, 60.9; H, 5.1; N, 10.3; S, 11.7. $C_{14}H_{14}N_2O_2S$ requires C, 61.3; H, 5.1; N, 10.2; S, 11.7%).

EXAMPLE 2a

(3R,6R,7R)-3-Hydroxy-7-phenylacetamido-cepham (1R,5R,2¹R and S)-3-Benzyl-7-(oxiran-2¹-ylmethyl)-4,7-diaza-6-oxo-2-thiabicyclo-[3,2,0]-hept-3-ene (2.0 g., 7.3 mmole) was dissolved in 50% aqueous acetic acid (30 ml.) and kept at 23° for 2.75 hours. The reaction mixture was partitioned between ethyl acetate and water and the organic phase washed with water and brine and dried over sodium sulphate. Removal of the ethyl acetate gave a solid (1.89 g.) which was extracted with a 1:1- mixture of ethyl acetate and chloroform (16 ml.). The solvent-soluble material (0.9 g.) was chromatographed on silica gel with ethyl acetate as solvent. The fractions containing the major product were combined and evaporated to give (3R,6R,7R)-3-hydroxy-7-phenylacetamidocepham (0.41 g., 19%), m.p. 175.7° (Mettler), $[\alpha]_D^{23}$ + 210° (c, 1.03, N,N-dimethylformamide), $\lambda_{max}^{EtOH}$ 252, 257.5 and 264 nm ($\epsilon$ 205, 234, and 175), $\nu_{max.}$ (Nujol) 3630 (OH), 3450 (NH), 1756 ($\beta$-lactam), 1692 and 1516 cm$^{-1}$ (CONH), NMR (d$_6$-DMSO, $\tau$) 0.95 (d, J 9 Hz, NH), 2.65 (C$_6$H$_5$), 4.45 (d, J 5 Hz, OH), 4.66 (dd, J 4.5 and 9 Hz, 7-H), 5.09 (d, J 4 Hz, 6-H), 6.13 and 7.3 (complex, 4-CH$_2$), 6.46 (complex, Ph CH$_2$ and 3-CH), 7.1 to 7.4 (complex 2-CH$_2$). (Found: C, 57.2; H, 5.5; N, 9.8; S, 11.0. C$_{14}$H$_{16}$N$_2$O$_3$S requires C, 57.5; H, 5.5; N, 9.6; S, 11.0%).

EXAMPLE 2b

(3S,6R,7R)-3-Hydroxy-7-phenylacetamidocepham

Continued elution (see Example 2a) with ethyl acetate gave (3S,6R,7R)-3-hydroxy-7-phenylacetamidocepham; m.p. 166.5° to 166.7° (Mettler) (from ethyl acetate), $[\alpha]_D^{21}$ + 194° (c, 1.16; CHCl$_3$). $\lambda_{max.}^{EtOH}$ 252, 257.5 and 263.5 nm ($\epsilon$, 200, 230, and 170), $\nu_{max.}$ (Nujol) 3402 (OH), 3340 (NH), 1744 ($\beta$-lactam), and 1676 and 1530 cm.$^{-1}$ (CONH), NMR (d$_6$-DMSO, $\tau$) 1.08 (d, J 9 Hz, NH), 2.71 (C$_6$H$_5$), 4.73 (dd, J 4.5 and 9 Hz, 7-H), 5.09 (OH), 5.15 (d, J 4 Hz, 6-H), 6.45 (PhCH$_2$-), 6.2 to 7.3 (comlex; 2-CH$_2$, 3-CH and 4-CH$_2$). (Found: C, 57.4; H, 5.5; N, 9.5; S, 10.9. C$_{14}$H$_{16}$N$_2$O$_3$S requires C, 57.5; N, 5.5; N, 9.6; S, 11.0%).

Example 3a

(6R,7R)-3-Keto-7-phenylacetamidocepham

To a solution of (3R,6R,7R)-3-hydroxy-7-phenylacetamidocepham (1.4 g., 4.78 mmole) in dimethylsulphoxide (25 ml.) was added acetic anhydride (5 ml.). The reaction mixture was kept at 22° for 16 hours, diluted with ethyl acetate, and washed with water and sodium bicarbonate solution. Removal of the solvent gave a crystalline solid (1.23 g.) which was dissolved in benzene:ethyl acetate: chloroform = 2:2:1 (10 ml.) and adsorbed on a 10 $\times$ 2.5 cm column of silica gel. Elution with the same solventmixture gave (6R,7R)-3-oxo-7-phenylacetamidocepham (0.33 g., 23%), as plates from isopropyl alcohol, m.p. 183.4° (Mettler), $[\alpha]_D^{22}$+472.5° (c, 1.0, N,N-dimethylformamide), $\lambda_{max}^{EtOH}$ 250, 257, 263 nm ($\epsilon$ 280, 280, 190), $\nu_{max}^{nujol}$ 3287 (NH), 1764 ($\beta$-lactam), 1712 (ketone), and 1650 and 1524 cm$^{-1}$ (CONH), NMR (d$_6$-SMSO, $\tau$) 0.85 (d, J 9 Hz, NH), 2.67 (C$_6$H$_5$), 4.61 (dd, J 4.5 and 9 Hz, 7-H), 4.86 (d, J 4 Hz, 6-H), 6.60 and 6.1 (q, J 19 Hz, 2-CH$_2$), 6.10 and 6.86 (q, J 15 Hz, 4-CH$_2$), 6.39 (Ph.CH$_2$). (Found: C, 57.4; H, 4.9; N, 9.6; S, 10.9. C$_{14}$H$_{14}$N$_2$O$_3$S requires C, 57.9; H, 4.9; N, 9.6; S, 11.0%).

Example 3b

(6R,7R)-3-Keto-7-phenylacetamidocepham

A solution of (3R,6R,7R)-3-hydroxy-7-phenylacetamido cepham (6.0 g., 20.5 mmole) and dicyclohexylcarbodiimide (11.65 g., 56.6 mmole) in dimethyl sulphoxide (50 ml.) was treated with pyridine trifluoroacetate (1.37 g., 7.1 mmole) and the mixture was stirred at 26° for 1½ hours. Acetic acid (6 ml.) and water (2 ml.) were added and the mixture was stirred for 30 minutes before being diluted with ethyl acetate (250 ml.) and filtered to give dicylohexylurea (10.04 g., 79%) as colourless prisms. The filtrate was washed with saturated aqueous sodium hydrogen carbonate (2 $\times$ 200 ml.), dried, and evaporated under reduced pressure to give a brown solid (7.65 g.). The solid was refluxed with acetonitrile (100 ml.) for 5 minutes, filtered to give more dicyclohexyl urea (0.4 g., 3.2%) and the filtrate was evaporated under reduced pressure. The resulting brown solid was dissolved by heating under reflux with isopropyl alcohol (150 ml.) for 15 minutes and on cooling, crystals of (6R,7R)-3-keto-7-phenylacetamidocepham (3.6 g., 60.5% in two crops) separated out; m.p. and NMR were in agreement with standards.

EXAMPLE 3c

(6R,7R)-3-Keto-7-phenylacetamidocepham (3S,6R,7R)-3-Hydroxy-7-phenylacetamidocepham (29 mg.) in dimethylsulphoxide (1 ml.) was treated with acetic anhydride (0.2 ml.) After being kept at 24° for 16 hour the reaction mixture was partitioned between brine and ethyl acetate. Removal of the ethyl acetate gave (6R,7R)-3-keto-7-phenylacetamidocepham (22 mg.). T.l.c. and g.l.c. data were in agreement with those obtained on material prepared in Example 3a. EXAMPLE 3d

(6R,7R)-3-Keto-7-phenylacetamidocepham

A solution of (3R,6R,7R)-3-hydroxy-7-phenylacetamidocepham (0.5 g., 1.72 mmole) in anhydrous acidfree methylene chloride (15 ml.) containing anhydrous tetrahydrofuran (3 ml.) was treated with a solution of chromium trioxide/pyridine complex (1.3 g., 3 equivalents) in methylene chloride (30 ml.) at 21° for 1 hour. The reaction mixture was poured into excess dilute hydrochloric acid. After separation, the organic phase was washed with water, dried, and evaporated to an oil. Trituration with ethyl acetate and ether gave the title compound (0.095 g., 19%) m.p. 174° to 177° (cap.) $\nu_{max.}$ (bromoform, Unicam) 3430 (NH), 1770 ($\beta$-lactam), 1735 (ketone), 1678 and 1515 cm.$^{-1}$ (amide).

EXAMPLE 4

(3R,4R)-4-(3'-Bromoacetonylthio)-3-phenylacetamidoazetidin-2-one

To a stirred suspension of (1R,5R)-3-benzyl-4,7-diaza-6-oxo-2-thiabicyclo-[3,2,0]-hept-3-ene (1.09 g., 5 mmole) in acetic acid (30 ml.) and water (25 ml.) was added 1,3-dibromoacetone (8.2 g., 38 mmole). After a period of 1 hr. at 22° the resultant solution was partitioned between water and ethyl acetate. The organic phase was washed with water, sodium bicarbonate solution, and brine, and dried over sodium sulphate. Removal of the solvent gave an oil which was triturated with isopropyl ether to give a gum (2.0 g.). Crystallisation from ethyl acetate gave (3R,4R)-4-(3'-bromoacetonylthio)-3-phenylacetamidoazetidin-2-one (0.84 g., 45.4%). A sample was purified by chromatography in chloroform on silica gel, m.p. 104° to 106° (cap., decomp.), $[\alpha]_D^{23}$ + 37° (c 0.95, dimethylsulphoxide), $\nu_{max}$. (Nujol) 3310 and 3250 (NH), 1755 ($\beta$-lactam), 1740 ($\alpha$-bromoketone), 1668 and 1550 cm.$^{-1}$ (CONH), NMR. ($d_6$-DMSO, $\tau$) 1.03 (d,J9 Hz, NH), 1.17 (NH), 2.66 ($C_6H_5$), 4.70 (dd, J 4.5 and 9 Hz, 7-H), 5.05 (d, J 4.5 Hz, 6-H), 5.58 ($CH_2Br$), 6.36 (S.$CH_2$), 6.42 (Ph$CH_2$). (Found: C, 45.2; H, 4.3; Br, 20.6; N, 7.4; S, 8.6. $C_{14}H_{15}BrN_2O_3S$ requires C, 45.3; H, 4.1; Br, 21.5; N, 7.6; S, 8.6%).

EXAMPLE 5

(6R,7R)-3-Keto-7-phenylacetamidocepham

A solution of (3R,4R)-4-(3'-bromoacetonylthio)-3-phenylacetamidoazetidin-2-one (1 g., 2.7 mmole) in acetone (50 ml.) with potassium carbonate (2 g., 14.5 mmole) was stirred at 4° for 16 hours and at 22° for 4 hours. The mixture was filtered and evaporated under reduced pressure. The resulting gum was chromatographed on silica gel (10 × 4 cm.) with Analar chloroform as solvent to give a pale-yellow foam. Crystallisation from ethyl acetate gave (6R,7R)-3-keto-7-phenylacetamidocepham (0.1 g., 12.5%). M.p. I.R. and NMR in agreement with standard obtained from material prepared in Example 3.

We claim:

1. 3-Hydroxy and 3-oxo-7-amino and protected amino-(6R, 7R)-cephams having the formula:

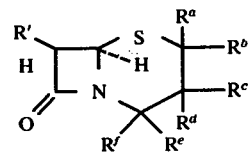

wherein $R^1$ represents a free or protected amino group; $R^a$, $R^b$, $R^e$ and $R^f$ each represent a hydrogen atom, and either $R^c$ represents a hydroxy group and $R^d$ represents a hydrogen atom or $R^c$ and $R^d$ together represent an oxygen atom.

2. Compounds as claimed in claim 1 having at the 7-position a protected amino group wherein said protected amino group is a group RCONH- where RCO is an acyl group containing 1 to 20 carbon atoms.

3. Compounds as claimed in claim 2 wherein R represents a benzyl group.

4. A compound selected from the group:
   (3R, 6R, 7R)-3-hydroxy-7-phenylacetamidocepham;
   (3S, 6R, 7R)-3-hydroxy-7-phenylacetamidocepham; and
   (6R, 7R)-3-keto-7-phenylacetamidocepham.

* * * * *